Aug. 6, 1957 A. A. BOOS Plant Pat. 1,626
PEACH TREE
Filed Dec. 21, 1955
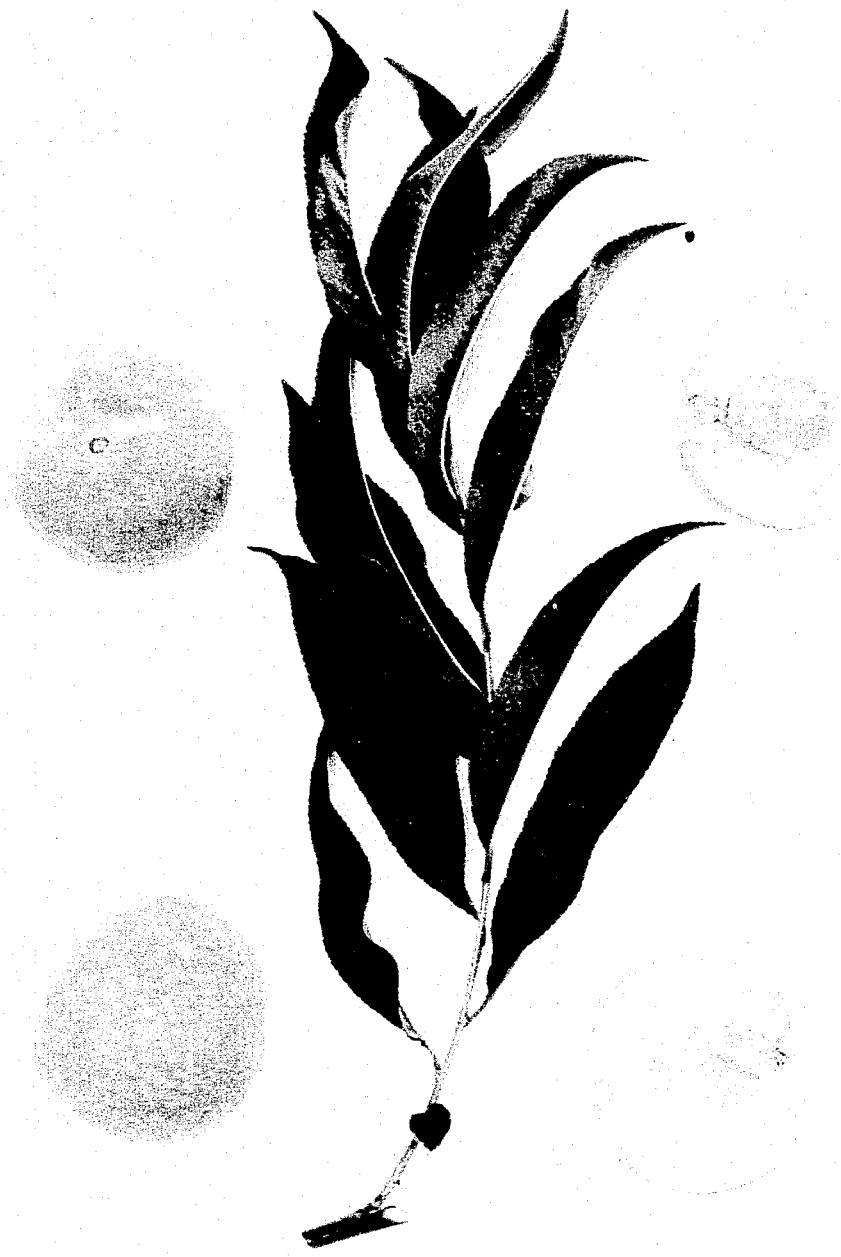
ALBERT A. BOOS
INVENTOR
HUEBNER, BEEHLER,
WORREL & HERZIG
ATTORNEYS
BY Richard M. Worrel United States Patent Office Plant Pat. 1,626
Patented Aug. 6, 1957

1,626

PEACH TREE

Albert A. Boos, Reedley, Calif.

Application December 21, 1955, Serial No. 554,598

1 Claim. (Cl. 47—62)

The present discovery relates to a peach tree and more particularly to a peach tree which originated as a bud sport of the Redhaven, an unpatented variety developed by Michigan State University.

The sport was discovered by me in my orchard and has been reproduced by me at 6699 South Buttonwillow, Reedley, county of Fresno, State of California by budding. The asexual reproduction of this new variety shows the subsequently described characteristics to be consistent and well established.

Not only is this new peach tree an offspring of the Redhaven but it is probably more closely similar to that variety than any other. It bears bright red splotched fruit having yellow flesh and being freestone when fully ripe but even then is frequently subject to some minor adherence of the flesh to the pit. Like the Redhaven, it ripens in June under the ecological conditions prevailing in the San Joaquin Valley. The flesh is firm and has a good flavor and the fruit has fuzz to the approximate extent of the Redhaven.

The new variety is characterized as to novelty when compared with the Redhaven by ripening seven to ten days earlier, bearing less heavily but having larger fruit, the fruit being more heavily splotched with a darker and brighter red, and the pit well varying from yellow to light pink as contrasted with the usual bright red pit well of the Redhaven. Additionally, the tree of the new variety is of narrower silhouette than the Redhaven under similar growing and pruning conditions, is somewhat more vigorous growing and is more erect in its growing habits. The blossoms are almost identical in appearance to those of the Redhaven but open a few days earlier. The unopened buds are considerably darker than those of the Redhaven but when opened there is only slight difference. The trees of the new variety leaf out a few days earlier than the Redhaven but this is not regarded as a marked or dependable distinction because the Redhaven trees with which comparison was made were somewhat older than the trees of the new variety. As the fruit matures, the fruit of the new variety usually colors earlier and the sutures thereof disappear earlier than in the Redhaven. The mature fruit is somewhat rounder than the Redhaven and usually of greater diameter normal to the suture plane than either transversely or longitudinally of the suture plane. The flavor of the fruit is more like the regular Elberta (unpatented) than like the Redhaven. In the autumn, the leaves are more yellow and not nearly as orange in color as the Redhaven.

The high color of the fruit of the new variety is quite similar to that of the Merrill Gem of Plant Patent No. 868 but is readily distinguished from the gem. For example, the fruit of the new variety is freestone while the gem is a cling. The new variety ripens a few days later than the gem. The flesh of the new variety is yellow and lacks the red mottling of the gem.

Comparison may also be made with the Merrill Beauty of United States Plant Patent No. 905. The color of the fruit of the subject variety is quite similar to the beauty but somewhat darker, brighter, and has more splotches. It colors earlier than the Merrill Beauty, a picking and shipping advantage, but ripens about the same time as the beauty when grown under similar conditions. The fruit is more nearly round than the beauty, and its pit well is yellow or yellowish brown at maturity as contrasted with the pink or red coloration of the pit well of the beauty at maturity.

In the accompanying drawing are shown several peaches and a twig bearing leaves of the new variety. The peaches are arranged so as to show a stem end, an apex, and a fruit divided on the suture plane with the pit removed.

The following detailed description generally follows the outline suggested by U. P. Hedrick in his book entitled "Systematic Pomology" published in 1925 and the color terminology is in accordance with the "Dictionary of Color" by Maerz and Paul, second edition.

*Tree*

General characteristics: Medium size, vigorous, upright, somewhat narrow in silhouette, hardy, productive, but not as heavily as the Redhaven, and a regular bearer.

Trunk: Medium stocky and medium smooth.

Branches: Similar to Redhaven varying in color from Autumn, Plate 8–A–12 with streaks of Burnt Umber, Plate 15–A–12.

Lenticels: Medium in size and number.

Leaves: Average length when mature approximately 6½ inches. Average width when mature about 1¾ inches. Large, acuminate, lanceolate, acutely pointed, smooth surfaced, infrequent glands, peripherally serrated, and only slightly wavy. Surfaces proximate Amulet, Plate 30–L–7 with veins approximately Plate 13–J–1.

Petiole: Longitudinally grooved and of medium length, approximately ½ inch when mature, and frequently with single glands. Blend in color from Plate 13–J–1 to Gold Pheasant, Plate 13–L–12 to Sage Green, Plate 22–J–5.

Buds: Medium size, medium length, obtuse, pubescent, similar to Redhaven but much darker pink.

Blossoms: Nearly identical to Redhaven but slightly darker pink and few days earlier than Redhaven. Self-pollinating.

*Fruit*

The fruit is of high quality, of attractive color and ships and stores well.

Ripening period: In the San Joaquin Valley of California approximately June 7 to June 20. Seven to ten days ahead of the Redhaven, concurrently with Santa Rosa Plums (unpatented) and two or three days after gem of Plant Patent No. 868.

Size: Large with normal thinning. Longitudinal diameter 2⅝ to 3 inches. Diameter transversely in suture plane 2⅝ to 3 inches. Diameter transversely and normal to suture plane 2¾ to 3¼ inches.

Form: Uniform, symmetrical, globose.

*Suture.*—Shallow and nearly disappears at maturity.

*Stem end.*—Retuse, shallow, abrupt. Slightly elongated in suture plane.

*Dorsal surface.*—Almost perfectly spherical.

*Ventral surface.*—Rounded and only very slightly lipped.

*Apex.*—Slightly flattened with small apical pistil point.

Flesh: Relatively firm, excellent flavor, similar to the Burbank July Elberta of Plant Patent No. 15.

*Color.*—Yellow of approximately Plate 9–I–4 with Capucine Y, Plate 9–K–8 around the edges and toward the stem end and with splotches of white adjacent to the pit well. Pit well almost identical to flesh and occasionally varying to Burnt Orange, Plate 3–E–12 to Plate 9–J–6 to Capucine Y, Plate 9–K–8. Approximately 1⅝ inches long and 1⅜ inch suture plane.

*Amygdalin.*—Undetected.

*Juice.*—Abundant and rich.

*Texture.*—Firm and crisp.

*Fibers.*—Few and tender.

*Ripens.*—Rather evenly.

*Flavor.*—Mildly acid and sweet somewhat similar to the regular Elberta.

*Aroma.*—Fragrant.

*Eating quality.*—Excellent.

Skin: Medium thickness and strength, tenacious to flesh except where overripe or bruised, no noticeable tendency to crack and heavy pubescence.

*Color.*—Terra Cotta (Algonquin), Plate 4–D–12 with small irregular splotches of Capucine Y, Plate 9–K–8 and larger more elongated splotches of Capucine Y, Plate 9–K–8 around the stem end. At maturity the fruit is unusually bright and colorful.

Stone: Free when fruit is fully ripe but rather tightly adherent before maturity.

*Size.*—Medium, average length approximately 1½ inches, average width approximately 1¼ inches and average thickness approximately ⅝ inch.

*Fibers.*—Minimum.

*Form.*—Obovate, tip rounded and only slightly acuminate usually having pronounced blade on ventral edge.

*Hilum.*—Oval.

*Surfaces.*—Grooved and pitted.

*Color.*—Light tan.

*Tendency to split.*—Not detected.

Use: Excellent for dessert, culinary uses, and shipping.

Keeping quality: Good.

The subject peach tree and its fruit may vary in minor particulars due to climatic, soil and other environmental variations but has been described as observed under cultivation in the San Joaquin Valley of California.

Having thus described my discovery, I claim:

A new and distinct variety of peach tree, substantially as illustrated and described bearing large, firm, red splotched freestone fruit having yellow flash and being characterized as to novelty when compared with the Redhaven to which it appears to be most similar by ripening seven to ten days earlier, bearing less heavily but having larger fruit, the fruit being more heavily splotched with a darker and brighter red, and the pit well varying from yellow to light pink as contrasted with the usual bright red pit well of the Redhaven.

No references cited.